United States Patent [19]

Chen et al.

[11] Patent Number: 4,468,371

[45] Date of Patent: Aug. 28, 1984

[54] IMMUNOASSAY TEST SLIDE

[75] Inventors: Anthony B. Chen, Hayward; Richard A. Harte, Redwood City; Nancy K. Kaufman, Belmont, all of Calif.

[73] Assignee: Daryl Laboratories, Inc., Santa Clara, Calif.

[21] Appl. No.: 399,920

[22] Filed: Jul. 19, 1982

[51] Int. Cl.³ .................. G01N 33/54; G01N 35/00; G01N 35/02

[52] U.S. Cl. .................................. 422/102; 422/65; 435/293; 435/300; 436/809

[58] Field of Search ............... 435/293, 300; 422/102, 422/65; 436/809

[56] References Cited

U.S. PATENT DOCUMENTS

| | | | |
|---|---|---|---|
| 2,561,339 | 7/1951 | Chediak | 435/300 X |
| 2,956,931 | 10/1960 | Goldberg | 435/293 X |
| 3,829,223 | 8/1974 | Hamel | 422/102 X |
| 3,932,141 | 1/1976 | Beall | 422/102 |
| 4,038,149 | 7/1977 | Liner | 435/300 |
| 4,154,795 | 5/1979 | Thorne | 435/300 X |
| 4,246,339 | 1/1981 | Cole | 422/102 X |
| 4,263,256 | 4/1981 | Morle | 422/102 X |
| 4,299,920 | 11/1981 | Peters | 435/300 X |

Primary Examiner—Sidney Marantz
Attorney, Agent, or Firm—Kolisch, Hartwell, Dickinson & Anderson

[57] ABSTRACT

A test slide for the performance of a series of immunoassay tests having: a substantially elongated and thin body of solid material; a plurality of individual test wells formed in said body; alignment means formed in said body in association with each of said wells; and movement facilitating means formed in said body; said slide being suitable for insertion into an automated testing device, said slide moving by said movement facilitating means, and said wells being aligned for detection by said alignment means.

8 Claims, 7 Drawing Figures

IMMUNOASSAY TEST SLIDE

BACKGROUND OF THE INVENTION

1. Field of the Invention

The present invention relates generally to test slides for performing immunoassays and more particularly to an immunoassay test slide suitable for use in immunoassay testing which contains a series of test wells each having an immunosubstrate layer formed therein.

2. Description of the Prior Art

Immunoassay test slides having a series of test wells formed therein have been known in the industry for many years. Such test slides contain wells of varying shapes and sizes and are suitable for differing test procedures. Thus the prior art contains a test well shape consisting of a rounded bottom with diverging sidewalls, a test well shape consisting of a flat bottom and vertical sidewalls, and a test well shape consisting of a rounded dish shape having curved sidewalls.

In recent years, it has been found that immunoassay test results may be enhanced through the utilization of an immunosubstrate. The immunosubstrate serves to provide substantially increased numbers of binding sites for immunoreagents utilized in the test procedures. The enhanced binding capacity has created greater sensitivity to immunoassay tests utilizing immunosubstrates.

It therefore appeared innovative to place an immunosubstrate layer within individual test wells of the prior art test slides in order to enhance test results obtained therefrom. However, when tests were performed by the instant inventors utilizing an immunosubstrate in the various prior art test wells, inconsistent and inaccurate results were often obtained. It appeared that immunoreagents within the immunosubstrate layer gravitated to the sides of test wells having vertical sides. Test wells having rounded bottoms performed poorly and inconsistently for no obvious reason. It is the inventors hypothesis that the manner in which the immunosubstrate dries after wetting and the possible gravitation of immunoreagents during the drying process to particular areas of the immunosubstrate layer, such as to a ring towards the edge of the vertically sided well, contribute to the poor and unreliable results.

SUMMARY OF THE PRESENT INVENTION

It is therefore a primary objective of the present invention to provide an optimally shaped test well for performing immunoassays.

It is another objective of the present invention to provide an immunoassay test slide having a series of optimally shaped test wells formed therein for the rapid and accurate performance of immunoassay tests.

It is a further object of the present invention to provide an immunoassay test slide which is formed for automated testing within a immunoassay testing device.

The optimally shaped test well of the present invention has a flat bottom and diverging side walls. The test well has sufficient depth to contain an immunosubstrate layer and liquid immunoreagents which will be placed in the test well to react within the immunosubstrate layer.

The immunoassay test slide of the present invention contains a series of said optimally shaped test wells. Further embelishments of the test slide which aid in its utilization in an automated testing device include an edge formed as a rack for interaction with a pinion gear within the testing device and notches formed in an edge thereof for the accurate alignment of individual test wells with testing components within the testing device.

An advantage of the present invention is that accurate, sensitive and reproducible results are now obtainable utilizing test wells of the particular shape described herein along with suitable immunosubstrate materials.

Another advantage of the test slide of the present invention is that it may be utilized in an automated testing device such that accurate results for a series of tests may be obtained rapidly and inexpensively.

These and other objects and advantages of the present invention will no doubt become apparent to those of ordinary skill in the art after having read the following detailed description of the preferred embodiments which are illustrated in the several figures of the drawing.

IN THE DRAWING

DESCRIPTION OF THE PREFERRED EMBODIMENT

Figure 1:
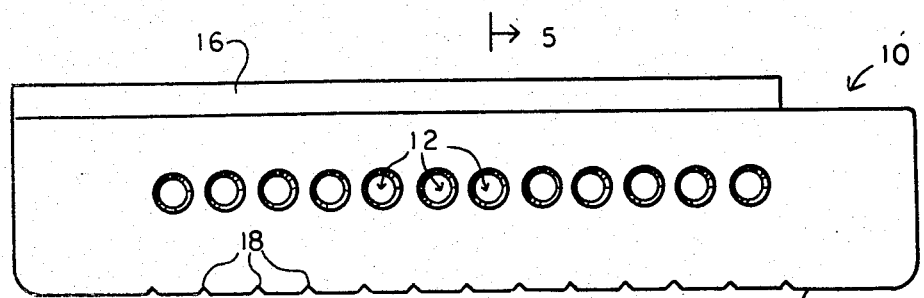
FIG. 1 is a top plan view of the immunoassay test slide of the present invention.
Figure 2:
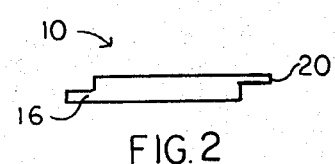
FIG. 2 is a left side elevational view of the immunoassay test slide shown in FIG. 1.
Figure 3:
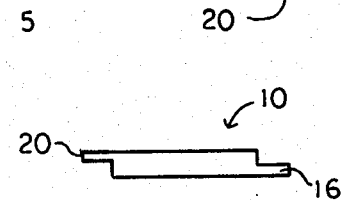
FIG. 3 is a right side elevational view of the immunoassay test slide shown in FIG. 1.

As depicted in FIGS. 1, 2 and 3, the preferred embodiment of the immunoassay test slide of the present invention 10 is basically a long thin strip of material having a series of test wells 12 formed therein. A suitable material is a polystyrene plastic however, other materials may be substituted therefore. When viewed from above, as in FIG. 1, it is seen that the test wells 12 are evenly spaced in a linear manner throughout the length of the slide 10. The spacing of the wells 12 from center line to center line is approximately 0.354 inches, such that standard industry microtiter equipment may be utilized therewith.

Figure 4:
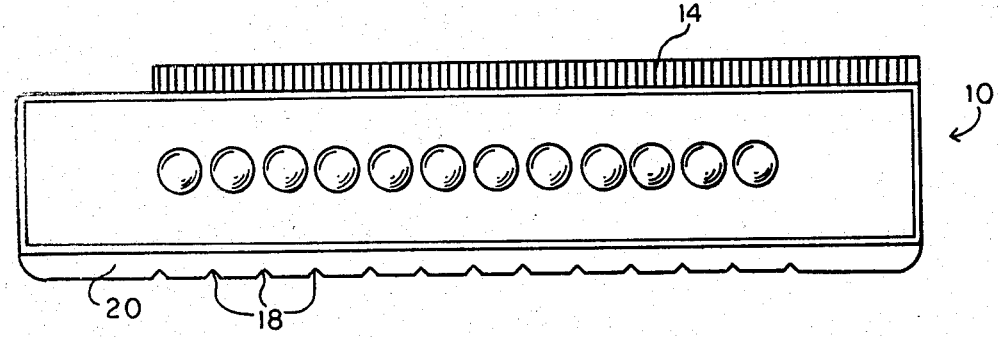
FIG. 4 is a bottom plan view of the immunoassay test slide of the instant invention.

The preferred embodiment of the immunoassay test slide 10 is formed for utilization in an automated testing system, not shown. The basic elements of the slide 10 which permit its movement within the automated testing system are a rack 14 which is formed along one of the elongated edges 16 of the slide 10. The depiction of the rack 14 in FIGS. 4, 5 and 6, will aid in the understanding of this feature. The rack 14 is formed for engagement with a pinion gear within an automated testing device to permit the controlled movement of the slide 10 within the automated testing device. The invention is not to be limited to only this type of rack 14 for the movement of the slide.

To accomplish the accurate alignment of individual test wells 12 within an automated testing device a series of notches 18 are formed in the other elongated edge 20 of the slide 10. An enhanced understanding of the notches 18 in edge 20 is to be gained from FIGS. 4, 5 and 7. Each of the notches 18 is formed in a prearranged accurate alignment with the wells 12 such that when the slide 10 is inserted within an automated testing device a suitable sensing device can detect the presence of a notch 18 along edge 20 to accurately align each individual test well 12 with a test detection system within the automated testing device. It is crucial to the creation of accurate and reproducible results from an automated test system utilizing the slide 10 that each test well be accurately and identically aligned relative to the test detection system within the automated testing device. The instant invention is not to be limited to the type of alignment system described herein, as equivalent systems may be easily substituted therefor.

Figure 5:
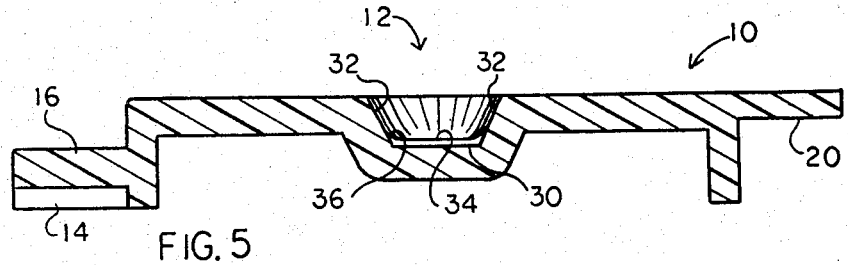
FIG. 5 is a cross-sectional view of the immunoassay test slide shown in FIG. 1, taken along lines 5—5 of FIG. 1 and depicts details of the test well formed therein.
Figure 6:
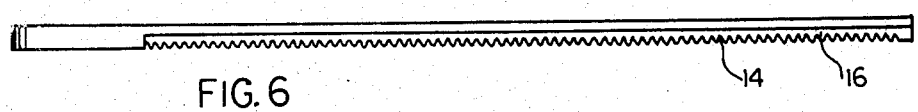
FIG. 6 is a rear elevational view of the immunoassay test slide shown in FIG. 1.
Figure 7:
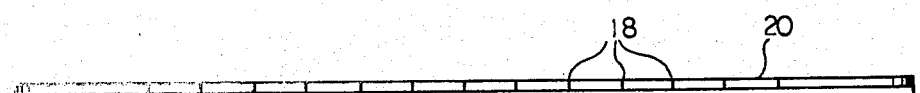
FIG. 7 is a front elevational view of the immunoassay test slide shown in FIG. 1.

A detailed depiction of the shape of each test well 12 of the slide 10 is presented in FIG. 5. As depicted therein, each test well is formed with a flat bottom 30 and has diverging sidewalls 32. The acute angle between the plane of the base 30 and the sidewall 32 in the preferred embodiment is formed to be approximately 68°. In the preferred embodiment, the diameter of the upper opening of each test well is approximately 0.250 inches, the diameter of the flat bottom 30 of each test well is approximately 0.188 inches and the depth of each test well is approximately 0.080 inches.

An immunosubstrate layer 34 is shown in the test well 12 of FIG. 5. A typical immunosubstrate layer 34 would have a thickness of approximately 0.004 inches and would exhibit a slight creeping 36 up the diverging sides 32 of the test well 12. The immunosubstrate layer 34 is utilized to provide a substantially increased number of binding sites for immunoreagents utilized in performing tests within the test well 12. The utilization of an immunosubstrate greatly increases the sensitivity and accuracy of immunoassays.

The above-described test well of the preferred embodiment, having a flat bottom and diverging sidewalls, when used with an immunosubstrate, has demonstrated in testing that it provides test results which are more consistent and accurate than test results obtained using preexisting test wells of differing shapes and the identical immunosubstrate.

More specifically, one type of prior art test well, possessing a rounded bottom together with diverging sidewalls was examined. When an immunosubstrate, consisting of latex polymer bead emulsion in water, was placed in the bottom of this test well and testing was conducted, the results were inconsistent from test well to test well and generally inaccurate. The inventors are unsure of the precise reasons for the inconsistency and inaccuracy, but believe that the rounded bottom of the test well created a deep pocket of immunosubstrate material which dried more slowly than the outer regions. It is believed that the uneven drying resulted in uneven concentrations of immunoreagents within the immunosubstrate and produced the inconsistent and inaccurate results. Additionally, it is believed that the rounded geometry of the well inhibits effective washing of unbound reagents from the immunosubstrate prior to the testing thereof. This effect also would tend to create poor results.

Further testing was conducted utilizing the prior art test wells which have a flat bottom and vertical sidewalls; the identical immunosubstrate was utilized to form a layer therein. Again, inconsistent and inaccurate results were obtained, as compared with those of the preferred embodiment. The inventors are unsure of the cause of the poor results, but it appeared that substantial creeping of the immunosubstrate up the walls of the test well was occurring. It is hypothesized that the vertical test walls create a shielding or shadowing effect such that the optical instruments utilized to perform the immunoassay testing could not accurately detect immunoreagents which had crept up the side walls. Additionally, the vertical sidewalls appeared to inhibit effective washing of the outer edges of the immunosubstrate. This would tend to permit unbound reagents to remain in the immunosubstrate and lead to inconsistent and inaccurate results. Again, the inventors were uncertain of the cause of the poor results and confirmed that the test well shape of the preferred embodiment is substantially superior.

A third prior art test well in the shape of a fully rounded depression was also examined. Test results utilizing this prior art shape with the immunosubstrate also proved inconsistent and inaccurate. The inventors believe the source thereof to be the rounded bottom which creates uneven drying and difficulty of washing of the immunosubstrate in the bottom of the test well, as was described hereinabove.

The instant invention achieves consistent and accurate immunoassay testing results through the utilization of a specially shaped test well 12 having a flat bottom and diverging sidewalls. The placement of a series of such test wells 12 in the instant test slide along with the utilization of the alignment notches 18 and rack 14 permit the slide 10 to be utilized in an automated immunoassay testing system to produce accurate results rapidly and inexpensively.

Whereas the preferred embodiment of the present invention has been described above, it is contemplated that other alterations and modifications may become apparent to those skilled in the art after having read the above disclosure. It is therfore intended that the appended claims be interpreted as covering all such alterations and modifications as fall within the true spirit and scope of the invention.

What is claimed is:

1. A test slide for the performance of a series of immunoassay tests comprising
   a substantially elongated and thin body of solid material;
   a plurality of individual test wells formed in said body,
   alignment means formed in said body in association with each of said wells, and
   movement facilitating means formed in said body,
   said slide being suitable for insertion into an automated testing device, said slide moving by said movement facilitating means, and said wells being aligned for detection by said alignment means.

2. The test slide described in claim 1 wherein a horizontal cross-section of each of said test wells is substantially circular in shape.

3. The test slide of claims 1 or 2 wherein the acute angle formed between the plane of said bottom surface of each test well and its associated diverging sidewall is approximately 68°.

4. The test slide of claim 3 wherein each test well has a depth of approximately 0.080 inches, said bottom surface has a diameter of approximately 0.188 inches and the opening of each test well has a diameter of approximately 0.25 inches.

5. The test slide as described in claim 4 wherein an immunosubstrate layer is formed in the bottom of each said test well to aid in the performance of immunoassay testing.

6. The test well of claim 5 wherein said immunosubstrate layer has a thickness of approximately 0.004 inches.

7. A test slide for the performance of a series of immunoassay tests employing an automatic testing device comprising:
   a substantially elongated and thin body of solid material;
   a rack formed along one elongated edge of said body for engagement with an automatic testing device;
   a plurality of test wells substantially evenly spaced in a linear manner along the length of said body; and
   a plurality of notches formed in said body, each notch being positioned in alignment with a different one of said test wells, thereby to align the wells in the automatic testing device.

8. A test slide for the performance of a series of immunoassay tests comprising:
   a substantially elongated and thin body of solid material;
   a plurality of test wells formed in said body, each of said test wells having a substantially flat bottom with an immunosubstrate layer having a thickness of approximately 0.004 inches deposited thereon;
   diverging sidewalls joined to and extending away from said bottom surface;
   a rack formed along one elongated edge of said body for engagement with an automated testing device; and
   a plurality of notches formed in said body, each notch being positioned in alignment with one of said test wells, thereby to align said wells within the testing device.

* * * * *